United States Patent [19]

Fukui et al.

[11] Patent Number: 5,216,482
[45] Date of Patent: Jun. 1, 1993

[54] APPARATUS FOR EMISSION SPECTROCHEMICAL ANALYSIS

[75] Inventors: Isao Fukui, Uji; Shuzo Hayashi, Kyoto, both of Japan

[73] Assignee: Shimadzu Corporation, Kyoto, Japan

[21] Appl. No.: 483,628

[22] Filed: Feb. 23, 1990

[30] Foreign Application Priority Data

Jun. 8, 1989 [JP] Japan ................................. 1-145712

[51] Int. Cl.$^5$ ...................... G01J 3/30; G01N 21/63; G01N 21/67
[52] U.S. Cl. ..................................... 356/313; 356/318
[58] Field of Search ............................... 356/313, 318

[56] References Cited

U.S. PATENT DOCUMENTS

| | | | |
|---|---|---|---|
| 3,531,202 | 9/1970 | Wilkinson et al. | 356/313 |
| 4,393,327 | 7/1983 | Walters et al. | 356/313 |
| 4,898,466 | 2/1990 | Fukui et al. | 356/313 |

FOREIGN PATENT DOCUMENTS 0182344 10/1984 Japan ................................. 356/313

OTHER PUBLICATIONS

Bhaumik et al, "Stroboscopic Time-Resolved Spectroscopy", The Review of Scientific Instruments, vol. 36, #1, Jan. 1965, pp. 37-40.
Anon, "New Laser Microspectral Analyzer", Monthly Technical Review, vol. 20, #1, pp. 8-9, Jan. 1986.
Technical Digest, No. 35, Jul. 1974, Western Electric; T. H. Briggs et al.: "Direct Reading Laser Spectrometer", pp. 9-10.

Primary Examiner—F. L. Evans
Assistant Examiner—K. P. Hantis
Attorney, Agent, or Firm—Wegner, Cantor, Mueller & Player

[57] ABSTRACT

Apparatus for emission spectrochemical analysis of a sample containing elements to be analyzed, wherein the sample is cyclically excited with relatively high energy to vaporize the sample elements and successively with relatively low energy to cause the vaporized elements to emit light containing spectral lines characteristic of the elements, which spectral lines are detected by a plurality of photomultiplier tubes corresponding to the spectral lines, with a common negative high-voltage source connected to the dynodes of the photomultiplier tubes. The negative high-voltage source is controlled in such a manner that it supplies a negative high voltage to the dynodes of the photomultiplier tubes to activate the tubes only during the low-energy excitation of the sample.

4 Claims, 4 Drawing Sheets

APPARATUS FOR EMISSION SPECTROCHEMICAL ANALYSIS

BACKGROUND OF THE INVENTION

This invention relates generally to emission spectroscopy and more particularly to an apparatus for emission spectrochemical analysis which utilizes spark discharges or pulses of a laser beam.

There is known a method of emission spectrochemical analysis in which spark discharges or pulses of a laser beam are applied to a sample to be analyzed to cause the sample to emit light, which is analyzed spectroscopically. The method has the following problem: In emission spectrochemical analysis using spark discharge, it is customary to pretreat the surface of a sample to be analyzed by applying spark discharges to the sample surface before analysis is conducted so as to reduce the adverse influence of small scars and/or pinholes on or in the sample surface and/or foreign matter, thereby improving the precision of analysis. For example, for analysis of a sample for 5 seconds the sample must be pretreated with high-energy spark discharges for more than 10 seconds.

The spark discharges for pretreatment of a sample may be referred to as the "preparatory discharges", while the spark discharges for analysis may be referred to as the "analytic discharges".

The reason why the preparatory discharge and the analytic discharge are conducted separately is as follows: Although high-energy discharge has a great capacity for vaporizing a sample, the resulting background light is strong as compared with the spectral line intensity of the component elements of the sample, with resulting decrease in the sensitivity of analysis. Therefore, low-energy discharge is suitable for analysis itself. Thus, after high-energy preparatory discharges have been conducted on a sample for 5 to 10 seconds, several thousand low-energy analytic discharges are conducted to analyze the light from the sample.

If the energy for analytic discharge is too low, however, the amount of the sample components vaporized decreases and the intensity of the light of the spectral emission lines produced becomes weak, with resulting reduction of the sensitivity and precision of analysis. Therefore, a sufficient amount of the sample must be vaporized by analytic discharges, so that there is a limit to which the energy level of the analytic discharges can be lowered, with resulting difficulty in reducing the background light.

As mentioned above, the time required for preparatory discharges is longer than the time required for analytic discharges. The reason why this is so is that the position in the surface of a sample which is struck by each of the spark discharges produced in one operation of analysis is uncertain, so that the whole area of the sample surface must be treated beforehand by preparatory discharges. To improve the precision of analysis a longer period of time is required for preparatory discharge.

Since a sufficient amount of the sample must be vaporized in analytic discharge, the energy for analytic discharge cannot be reduced to a very low level, with resulting difficulty in reducing the background light and obtaining a high sensitivity.

The present inventors have once proposed a method of spectro-chemical analysis of a sample containing elements to be analyzed, in which high-energy pulses are cyclically applied onto a small area of a sample to vaporize the components of the sample from the small area thereof, and low-energy spark discharges are generated by a spark generator including an electrode facing the sample so as to be applied to the small area of the sample a predetermined period of time after the application of each high-energy pulse and during the time in which the vaporized components of the sample caused by the application of high energy remains between the sample and the electrode, and the light emitted by the sample vapor while the low-energy spark discharges are being conducted is spectroscopically measured.

The characteristic of the above-mentioned prior invention is that each and every one of the emissions of light from the sample being analyzed comprises a step of vaporizing the sample and that of analyzing the vaporized elements of the sample. With the method of the prior invention, it is possible to analyze a sample at a cleaned spot on the surface thereof by low-energy spark discharge without pretreatment by conventional preparatory discharge, and to obtain a high sensitivity due to the lowered background level. The circuit arrangement, however, is complicated. In the prior art arrangement the output from the measuring circuit is amplified and sampled by a switching circuit operated synchronously with each emission of light from the sample, and one measuring channel must be provided for each one of the spectral lines of the elements in the sample, and one switching circuit is required for each measuring channel, with resulting complication of the whole circuit arrangement.

Accordingly, the primary object of the invention is to simplify the circuit arrangement used in an apparatus for emission spectro-chemical analysis which uses a time resolution method of measuring the spectral intensity of light emissions from a sample caused by spark discharge pulses each comprising a high-energy and a low-energy portion.

SUMMARY OF THE INVENTION

Briefly stated, the apparatus of the invention comprises: means for cyclically exciting a sample with relatively high energy to vaporize the elements contained in the sample to be analyzed and successively with relatively low energy to cause the vaporized elements to emit light; means for dispersing the light emitted by the vaporized elements to produce a spectrum containing spectral lines characteristic of the elements; a plurality of photomultiplier tubes each so arranged as to receive the light of one of the spectral lines to produce a corresponding electrical signal; a negative high-voltage source; and means for controlling the negative high voltage source to impress a negative high voltage upon the dynodes of the photomultiplier tubes during the low-energy excitation of the sample, so that the photomultiplier tubes receive the light of the spectral lines to produce a corresponding electrical signal, while preventing the negative high voltage from being impressed upon the dynodes during the high-energy excitation of the sample.

The photomultiplier tubes are rendered inoperative by cutting off the negative high voltage impressed on the dynodes of the photomultiplier tubes. Since the common negative high-voltage source supplies a voltage to the dynodes of the photomultiplier tubes in the measuring channels, by switching on or off the negative high-voltage source it is possible to control the operation of the photomultiplier tubes in all the measuring channels simultaneously, so that a single switching circuit suffices, with resulting simplification of the circuit arrangement of the apparatus.

PREFERRED EMBODIMENTS OF THE INVENTION

Figure 1:
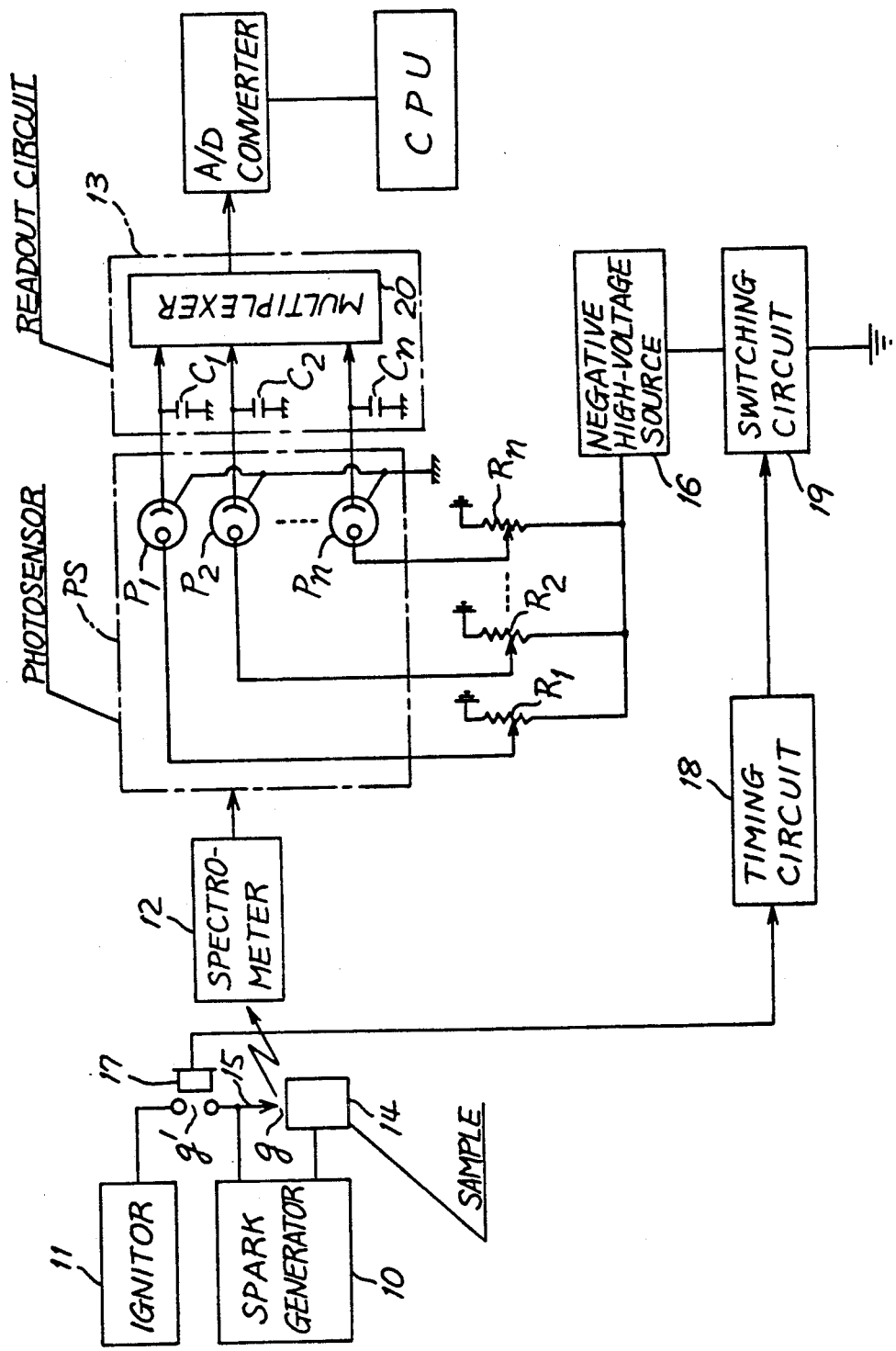
FIG. 1 is a block diagram schematically showing one embodiment of the invention.

FIG. 1 schematically shows one embodiment of the invention, which comprises a spark generator 10, an ignitor 11, a spectrometer 12, a photosensor PS and a readout circuit 13. A sample 14 to be analyzed and an electrode 15 are juxtaposed across an analytical gap g, with the ignitor 11 being connected thereto through a trigger spark gap g'.

The photosensor PS comprises a plurality of photomultiplier tubes $P_1, P_2, \ldots P_n$ arranged at predetermined wavelength positions on the spectral plane of the spectrometer 12. A negative high-voltage source 16 is connected to the dynodes of the photomultiplier tubes $P_1, P_2, \ldots P_n$ through sensitivity attenuators $R_1, R_2, \ldots R_n$, respectively. The readout circuit 13 comprises a plurality of capacitors $C_1, C_2, \ldots C_n$ and a multiplexer 20. The outputs of the photomultiplier tubes $P_1, P_2, \ldots P_n$ are stored in the capacitors $C_1, C_2, \ldots C_n$, respectively, the outputs of which are applied to a computer CPU through the multiplexer 20 and an analog/digital converter A/D.

A photodetector 17 is provided adjacent the trigger spark gap g' to detect the light caused by a trigger discharge and produce a detection pulse, which is applied to a timing circuit 18 which comprises a series combination of two one-shot circuits. The timing circuit 18 produces one output pulse having a certain width a certain period of time after the detection pulse from the photodetector 17 is applied thereto. The output pulse from the timing circuit 18 renders conducting a switching circuit 19 connected between the negative high-voltage source 16 and the ground.

The instant a spark is generated in the trigger spark gap g', a spark discharge is triggered in the analytical gap g of the spark generator 10. Therefore, by detecting the light caused to emit by a spark in the trigger spark gap g' and rendering the switching circuit 19 conducting for a predetermined period of time after a certain period of time, it is possible to sample the output from the photomultiplier tubes $P_1, P_2 \ldots P_n$ for a predetermined period of time during the discharge in the analytical gap.

Figure 2:
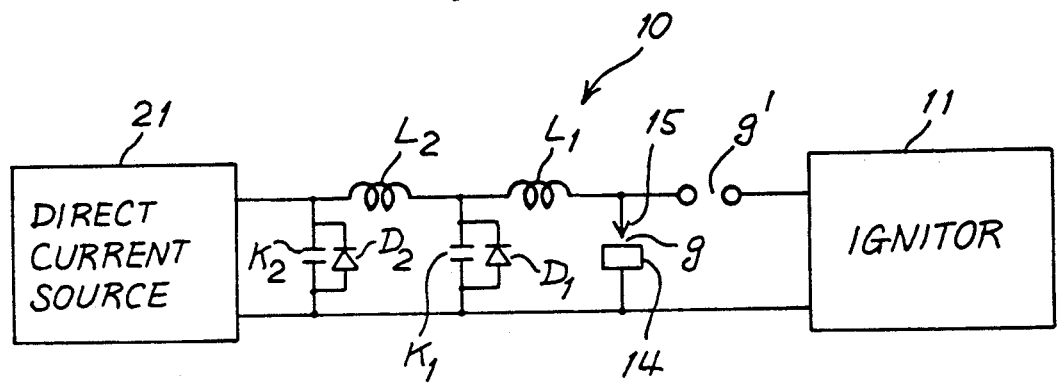
FIG. 2 is an electrical circuit diagram of a portion of FIG. 1.

FIG. 2 schematically shows an example of the spark generator 10, which comprises capacitors $K_1$ and $K_2$ for storing energy to be discharged, inductors $L_1$ and $L_2$ with a protective diode $D_1, D_2$ connected across each of the capacitors, and a direct current source 21 which charges the capacitors. The capacitor $K_1$ is connected to the analytical gap g through the inductor $L_1$, and the capacitor $K_2$ is connected to the analytical gap g through the series combination of inductors $L_1$ and $L_2$. The ignitor 11 is connected across the analytical gap g through the trigger spark gap g'.

When a discharge is generated in the trigger spark gap g' by a trigger pulse produced by the ignitor 11, the discharge current breaks the insulation of the analytical gap g and passes therethrough, whereupon the electric charge stored in the capacitors $K_1$ and $K_2$ is discharged through the analytical gap g. Since the electric charge of the capacitor $K_2$ is discharged through the inductors $L_1$ and $L_2$ connected in series, the discharge is conducted slowly. On the other hand, since the electric charge of the capacitor $K_1$ is discharged through the inductor $L_1$ only, the discharge is conducted quickly. In other words, the charge of the capacitor $K_1$ is discharged first and then the charge of the capacitor $K_2$ is discharged. With the capacitor $K_1$ of a larger capacity than that of the capacitor $K_2$, it is possible to supply a larger amount of energy from the first capacitor $K_1$ and a smaller amount of energy from the second capacitor $K_2$.

Figure 3:
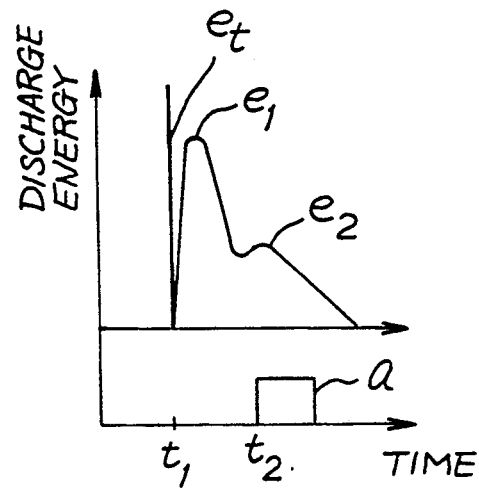
FIG. 3 is a waveform diagram for explanation of the operation of the apparatus of the invention.

FIG. 3 shows a waveform of a spark discharge generated in the analytical gap g. As shown in the figure each of the spark discharges generated in the analytical gap for one operation of analysis of a sample comprises a high-energy portion $e_1$ and a low-energy portion $e_2$ continuing from the high-energy portion. The timing circuit 18 receives the detection pulse when the photodetector 17 detects a trigger spark discharge $e_t$ at $t_1$ and after a period of time corresponding to the high-energy portion $e_1$ of the spark discharge in the analytical gap, the timing circuit 18 produces an output pulse a at $t_2$ to close the switching circuit 19 thereby to cause the negative high-voltage source 16 to activate the photomultiplier tubes $P_1 \sim P_n$, which detect the corresponding emission lines in the spectrum of the sample caused by the low-energy portion $e_2$ of the spark discharge and produce corresponding electrical signals.

In the above embodiment a negative high voltage is impressed on the dynodes of the photomultiplier tubes only during the low-energy excitation of the sample. It is also possible to prevent impression of a negative high voltage on the dynodes only during the high-energy excitation of the sample.

Figure 4:
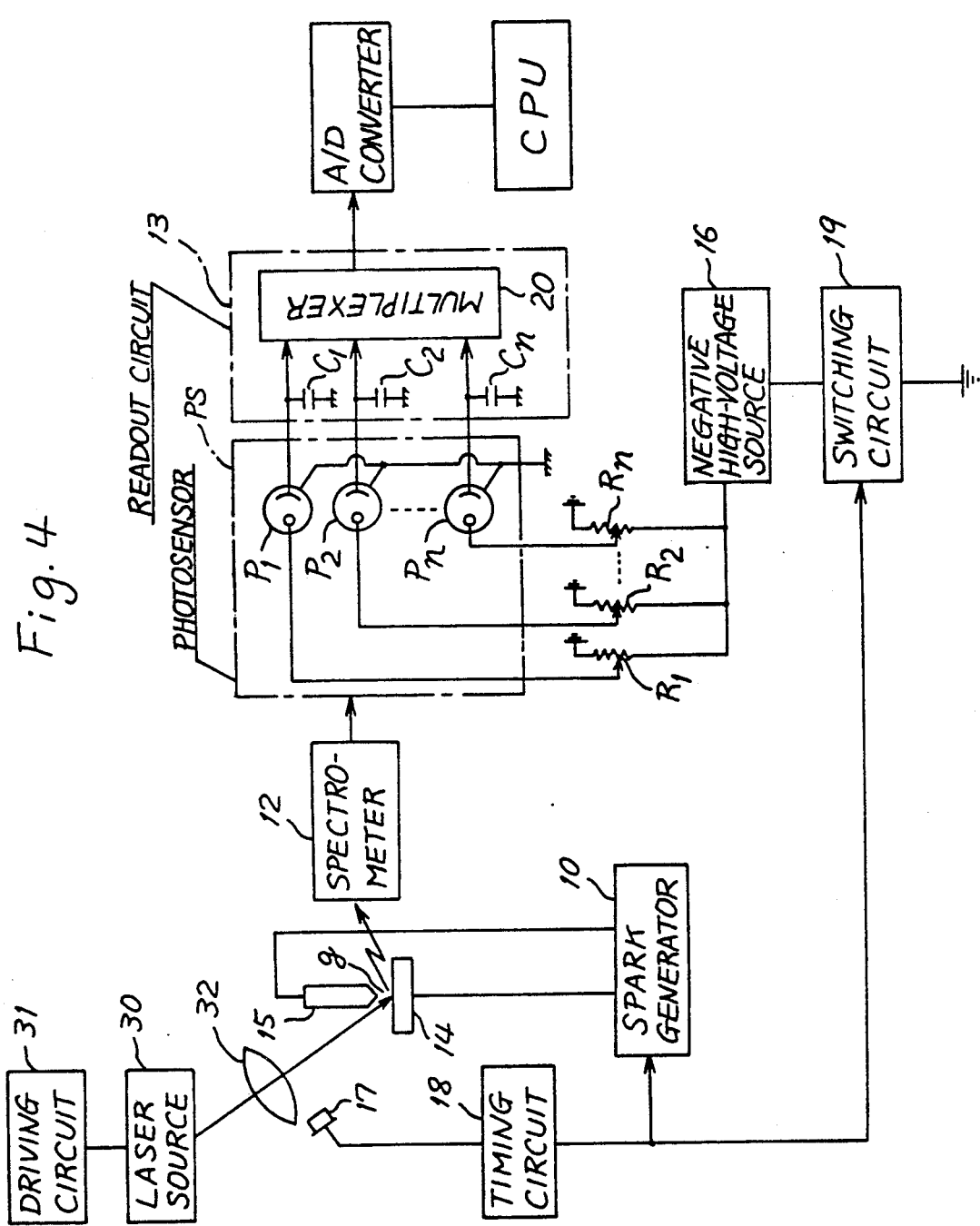
FIG. 4 is a block diagram schematically showing another embodiment of the invention.

FIG. 4 shows another embodiment of the invention, wherein a laser is used for vaporization of the sample. In FIG. 4 the same reference numerals as in FIG. 1 designate corresponding elements in FIG. 1, so that no explanation will be given to them except when necessary. The apparatus comprises a laser sourvce 30, a circuit 31 for driving the source 30 to produces pulses of high-energy laser beam at a predetermined cycle, and a lense 32 for focusing the laser beam onto a point on the surface of a sample 14 thereby to cause the material of the sample at the point to vaporize. At one side of the laser beam there is provided a beam detector 17 which detects each pulse of the laser beam to produce a detection signal, which triggers the timing circuit 18. Upon passage of a time preset in the timing circuit, the circuit produces an output signal to cause the spark generator 10 to produce a low-energy spark discharge in the analytical gap g between the sample 14 and the electrode 15. The output from the timing circuit 18 is also applied to the switching circuit 19 to close the circuit thereby to cause the negative high-voltage source 16 to activate the photomultiplier tubes $P_1 \sim P_n$ to operate in the same manner as described with reference to FIG. 1.

Figure 5:
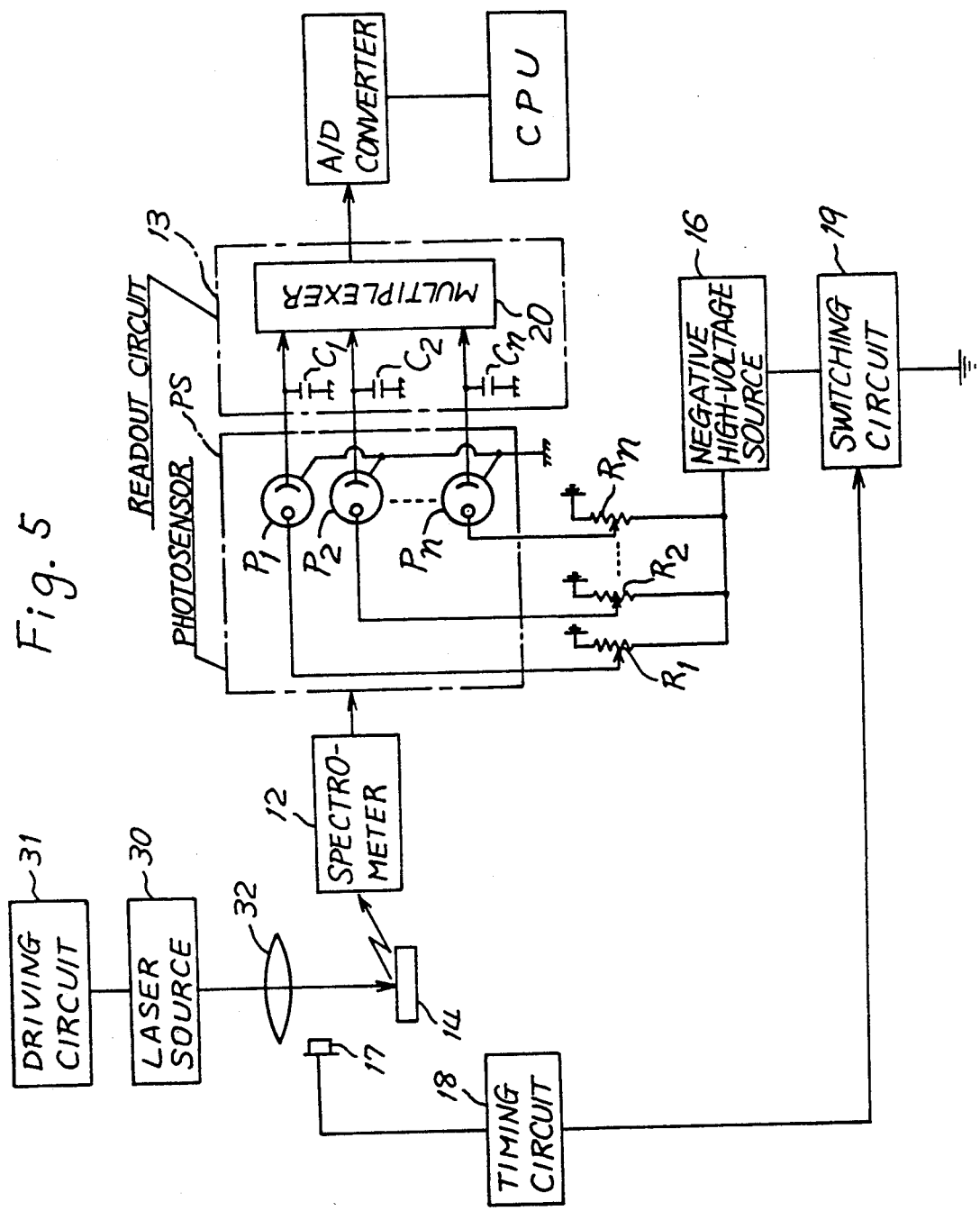
FIG. 5 is a block diagram schematically showing a third embodiment of the invention.

FIG. 5 shows a third embodiment of the invention wherein a laser is used for both high-energy and low-energy excitation of the sample. To this end, the driving circuit 31 in FIG. 5 is so designed as to cause the laser source 30 to produce laser pulses each having a high-energy portion and a low-energy portion such as shown in FIG. 3. Upon passage of a period of time corresponding to the high-energy excitation after the photodetector 17 detects the high-energy portion of each laser pulse, the timing circuit 18 produces an output pulse to close the switching circuit 19, whereupon the negative high-voltage source impresses a negative high voltage on the dynodes of the photomultiplier tubes $P_1 \sim P_n$ for activation thereof. In FIG. 5 the same reference numerals as in FIGS. 1 or 4 designate corresponding elements in FIGS. 1 or 4, and the readout circuit 13 operates in substantially the same manner as in the previous embodiments.

In accordance with the invention, it is possible to simplify the circuit arrangement for emission spectrochemical analysis of a sample wherein each of a number of emissions of light from the sample for one operation of analysis is caused by both high-energy and low-energy excitation of the sample, and no preparatory discharge need be conducted on the sample. Since high-energy excitation is immediately followed by low-energy excitation, it is possible with a smaller amount of energy than otherwise to cause the sample vapor to emit light, with resulting reduction of the background noise, improvement of the sensitivity and precision of analysis, and reduction of the manufacturing cost of the apparatus.

What we claim:

1. Apparatus for emission spectrochemical analysis of a sample containing elements to be analyzed, comprising:

means for cyclically exciting said sample with energy having a waveform including successive first and second peaks, said first peak being of relatively high energy to vaporize said elements contained in said sample and said second peak being of relatively low energy to cause a resulting vapor of said elements to emit light;

means for dispersing the light emitted by said vapor to produce a spectrum containing spectral lines characteristic of said elements;

a plurality of photomultiplier tubes, having a corresponding plurality of dynodes, with each of said photomultiplier tubes being so arranged as to receive the light of one of said spectral lines to produce a corresponding electrical signal;

a single negative high-voltage source connected to said dynodes;

means for controlling said negative high-voltage source to impress a negative high voltage substantially simultaneously upon said dynodes of said photomultiplier tubes during said low-energy excitation of said sample, so that said photomultiplier tubes receive said light of said spectral lines to produce a corresponding electrical signal, while preventing said negative high voltage from being impressed upon said dynodes during said high-energy excitation of said sample, said controlling means comprising a single, normally open, switching circuit connected between said negative high-voltage source and ground, means for detecting each cycle of said exciting means and producing a detection pulse in response thereto, and a timing circuit means for receiving said detection pulse and producing an output pulse to said switching circuit and causing said switching circuit to be closed during said low-energy excitation of said sample in response to said detection pulse, thereby causing said negative high-voltage source to activate said photomultiplier tubes.

2. Apparatus for emission spectrochemical analysis of a sample containing elements to be analyzed, comprising:

means for cyclically exciting said sample with energy having a waveform including successive first and second peaks, said first peak being of relatively high energy to vaporize said elements contained in said sample and said second peak being of relatively low energy to cause a resulting vapor of said elements to emit light;

means for dispersing the light emitted by said vapor to produce a spectrum containing spectral lines characteristic of said elements;

a plurality of photomultiplier tubes, having a corresponding plurality of dynodes, with each of said photomultiplier tubes being so arranged as to receive the light of one of said spectral lines to produce a corresponding electrical signal;

a single negative high-voltage source connected to said dynodes;

means for controlling said negative high-voltage source to impress a negative high voltage substantially simultaneously upon said dynodes of said photomultiplier tubes during said low-energy excitation of said sample, so that said photomultiplier tubes receive said light of said spectral lines to produce a corresponding electrical signal, while preventing said negative high voltage from being impressed upon said dynodes during said high-energy excitation of said sample, said controlling means comprising a single, normally closed, switching circuit connected between said negative high-voltage source and ground, means for detecting each cycle of said exciting means and producing a detection pulse in response thereto, and a timing circuit means for receiving said detection pulse and producing an output pulse, in response to said detection pulse, to said switching circuit and delaying said output pulse in order for said switching circuit to be opened during said high-energy excitation of said sample and thereby preventing said negative high-voltage source from activating said photomultiplier tubes.

3. An apparatus for emission spectrochemical analysis of a sample containing elements to be analyzed, comprising:

means for cyclically exciting said sample with successive first and second pulses of energy, said first energy pulse being of relatively high energy which is sufficient to vaporize said elements contained in said sample and said second energy pulse being of relatively low energy which is sufficient to cause a resulting vapor of said elements to emit light, said exciting means comprising a single laser producing said successive pulses of energy;

means for dispersing the light emitted by said vapor to produce a spectrum containing spectral lines characteristic of said elements;

a plurality of photomultiplier tubes, having a corresponding plurality of dynodes, with each of said photomultiplier tubes being so arranged as to receive the light of one of said spectral lines to produce a corresponding electrical signal;

a single negative high-voltage source connected to said dynodes;

means for controlling said negative high-voltage source to impress a negative high voltage substantially simultaneously upon said dynodes of said photomultiplier tubes during said low-energy excitation of said sample, so that said photomultiplier tubes receive said light of said spectral lines to produce a corresponding electrical signal, while preventing said negative high voltage from being impressed upon said dynodes during said high-energy excitation of said sample, said controlling means comprising a single, normally open, switching circuit connected between said negative high-voltage source and ground, means for detecting each cycle of said exciting means and producing a detection pulse in response thereto, and a timing circuit means for receiving said detection pulse and producing an output pulse to said switching circuit and causing said switching circuit to be closed during said low-energy excitation of said sample in response to said detection pulse, thereby causing said negative high-voltage source to activate said photomultiplier tubes.

4. An apparatus for emission spectrochemical analysis of a sample containing elements to be analyzed, comprising:

means for cyclically exciting said sample with energy having successive first and second peaks of energy, said first energy peak being of relatively high energy which is sufficient to vaporize said elements contained in said sample and said second energy peak being of relatively low energy which is sufficient to cause a resulting vapor of said elements to emit light, said exciting means comprising a laser producing a first energy pulse having said first energy peak of said relatively high energy and a spark generator producing a successive spark having said successive, second energy peak of said relatively low energy;

means for dispersing the light emitted by said vapor to produce a spectrum containing spectral lines characteristic of said elements;

a plurality of photomultiplier tubes, having a corresponding plurality of dynodes, with each of said photomultiplier tubes being so arranged as to receive the light of one of said spectral lines to produce a corresponding electrical signal;

a single negative high-voltage source connected to said dynodes;

means for controlling said negative high-voltage source to impress a negative high voltage substantially simultaneously upon said dynodes of said photomultiplier tubes during said low-energy excitation of said sample, so that said photomultiplier tubes receive said light of said spectral lines to produce a corresponding electrical signal, while preventing said negative high voltage from being impressed upon said dynodes during said high-energy excitation of said sample, said controlling means comprising a single, normally open, switching circuit connected between said negative high-voltage source and ground, means for detecting each cycle of said exciting means and producing a detection pulse in response thereto, and a timing circuit means for receiving said detection pulse and producing an output pulse to said switching circuit and causing said switching circuit to be closed during said low-energy excitation of said sample in response to said detection pulse, thereby causing said negative high-voltage source to activate said photomultiplier tubes.

* * * * *